US012765783B2

(12) United States Patent
Hilger et al.

(10) Patent No.: US 12,765,783 B2
(45) Date of Patent: Oct. 20, 2026

(54) METHOD FOR SIGNALING VITAL PARAMETERS AND/OR VITAL PARAMETER PATTERNS IN A VEHICLE

(71) Applicant: MERCEDES-BENZ GROUP AG, Stuttgart (DE)

(72) Inventors: Maximilian Hilger, Stuttgart (DE); Jürgen Schmidt, Köngen (DE); Arnulf Frisch, Weil Im Schoenbuch (DE); Jan Daßler, Kirchheim unter Teck (DE); Massi Jabbari, Aidlingen (DE)

(73) Assignee: MERCEDES-BENZ GROUP AG, Stuttgart (DE)

( * ) Notice: Subject to any disclaimer, the term of this patent is extended or adjusted under 35 U.S.C. 154(b) by 1027 days.

(21) Appl. No.: 17/784,165

(22) PCT Filed: Nov. 13, 2020

(86) PCT No.: PCT/EP2020/082116
§ 371 (c)(1),
(2) Date: Jun. 10, 2022

(87) PCT Pub. No.: WO2021/115726
PCT Pub. Date: Jun. 17, 2021

(65) Prior Publication Data

US 2023/0022765 A1 Jan. 26, 2023

(30) Foreign Application Priority Data

Dec. 11, 2019 (DE) ..................... 10 2019 008 563.9

(51) Int. Cl.
*A61B 5/0205* (2006.01)
*A61B 5/00* (2006.01)

(52) U.S. Cl.
CPC .......... *A61B 5/0205* (2013.01); *A61B 5/7405* (2013.01); *A61B 5/742* (2013.01); *A61B 5/7455* (2013.01); *A61B 5/746* (2013.01)

(58) Field of Classification Search
CPC ..... A61B 5/0205; A61B 5/7405; A61B 5/742; A61B 5/7455; A61B 5/746;
(Continued)

(56) References Cited

U.S. PATENT DOCUMENTS 5,979,586 A 11/1999 Farmer et al.
10,845,802 B2 11/2020 Stark et al.
(Continued)

FOREIGN PATENT DOCUMENTS

CN 106462027 A 2/2017
CN 109843174 A 6/2019
(Continued)

OTHER PUBLICATIONS

Paredes, Pablo E., et al. "Just Breathe: In-Car Interventions for Guided Slow Breathing" Proceedings of the ACM on Interactive, Mobile, Wearable and Ubiquitous Technologies, vol. 2, No. 1, Mar. 26, 2018, pp., https://doi.org/10.1145/3191760 (Year: 2018).*
(Continued)

*Primary Examiner* — Kristina M Deherrera
*Assistant Examiner* — Evan Mancini
(74) *Attorney, Agent, or Firm* — PATENT PORTFOLIO BUILDERS PLLC

(57) ABSTRACT

A method for signaling a measured and/or a predetermined vital parameter and/or vital parameter pattern for a vehicle occupant in a vehicle involves arranging a functional element set up to have a visual and/or audible and/or haptic effect on at least one vehicle occupant, and a measured
(Continued)

and/or a predetermined vital parameter and/or vital parameter pattern is signaled non-verbally by the functional element.

8 Claims, 1 Drawing Sheet

(58) Field of Classification Search
CPC ............ A61B 2505/09; A61B 5/02055; A61B 5/0816; A61B 5/165; A61B 5/168; A61B 5/18; A61B 5/7415; A61B 5/35; A61B 5/352; A61B 5/366; A61B 5/486; A61B 5/0006; A61B 5/0008; A61B 5/4836; B60W 2040/0872; B60W 2540/221; B60W 50/14; B60K 28/066
USPC ...................................................... 116/36, 30
See application file for complete search history.

(56) References Cited

U.S. PATENT DOCUMENTS

| | | | | |
|---|---|---|---|---|
| 2013/0302760 | A1* | 11/2013 | Welles | G09B 9/052<br>434/69 |
| 2014/0221781 | A1 | 8/2014 | Schrauf et al. | |
| 2018/0178808 | A1* | 6/2018 | Zhao | B60N 2/20 |
| 2018/0244288 | A1* | 8/2018 | Glaser | B60W 40/08 |

FOREIGN PATENT DOCUMENTS

| | | | | |
|---|---|---|---|---|
| DE | 10322458 | A1 * | 12/2004 | B60K 28/06 |
| DE | 102014219892 | A1 | 4/2016 | |
| DE | 102016005066 | A1 | 9/2016 | |
| DE | 102016207447 | A1 * | 11/2017 | |
| DE | 102017001320 | A1 | 8/2018 | |
| JP | 2002513351 | A | 5/2022 | |
| WO | 2014085302 | A1 | 6/2014 | |
| WO | WO-2015200224 | A2 * | 12/2015 | B60K 28/02 |

OTHER PUBLICATIONS

International Search Report mailed Feb. 15, 2021 in related/corresponding International Application No. PCT/EP2020/082116.
Office Action created Nov. 30, 2020 in related/corresponding DE Application No. 10 2019 008 563.9.
Written Opinion mailed Feb. 15, 2021 in related/corresponding International Application No. PCT/EP2020/082116.
Notification of Reason for Refusal dated Aug. 7, 2023 in related/corresponding JP Application No. 2022-532142.
Office Action dated Feb. 28, 2025 in related/corresponding CN Application No. 202080085961.0.
Office Action dated May 23, 2025 in related/corresponding EP Application No. 20808048.1.
Office Action dated Jul. 30, 2025 in related/corresponding CN Application No. 202080085961.0.

* cited by examiner

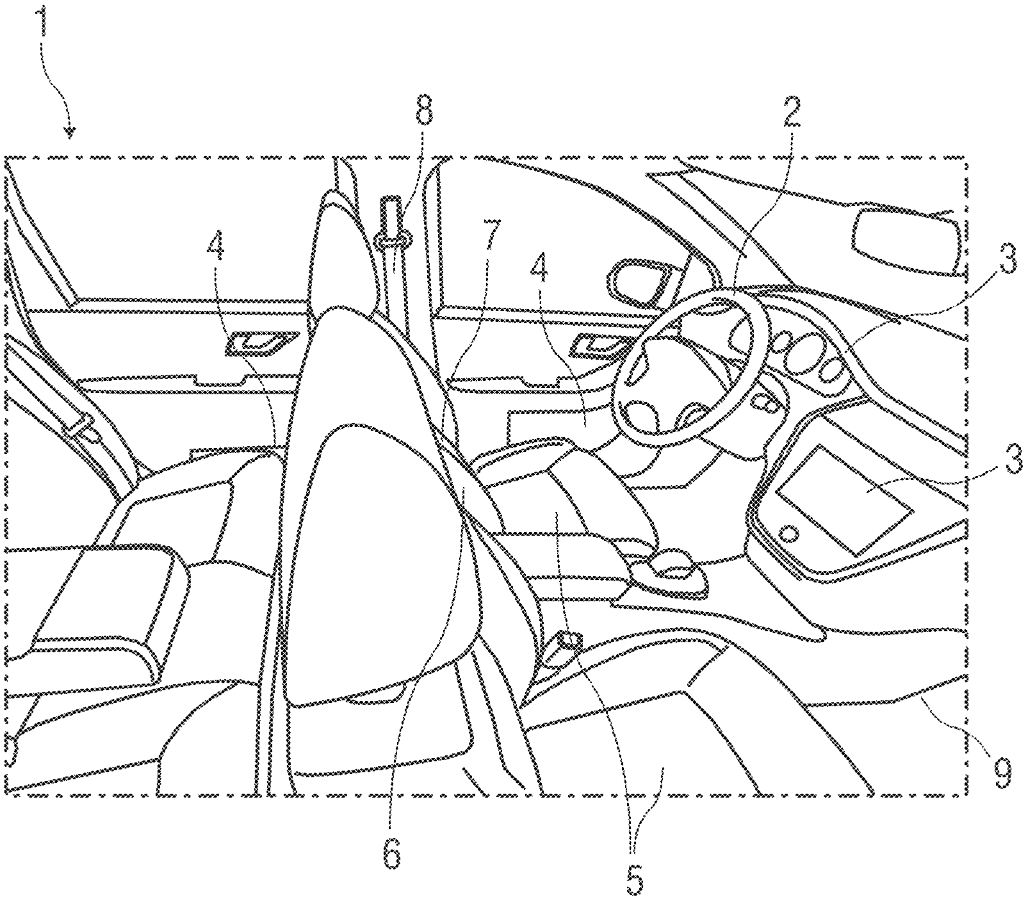
1
8
2
4
7
4
3
3
9
6
5

METHOD FOR SIGNALING VITAL PARAMETERS AND/OR VITAL PARAMETER PATTERNS IN A VEHICLE

BACKGROUND AND SUMMARY OF THE INVENTION

Exemplary embodiments of the invention relate to a method for signaling a measured and/or a predetermined vital parameter and/or vital parameter pattern for a vehicle occupant in a vehicle.

Printed publication DE 10 2017 001 320 A1 describes a method for operating a vehicle in which at least one actual vital parameter of at least one occupant is recorded and/or ascertained, wherein at least one vehicle comfort function is controlled and/or regulated depending on the recorded and/or ascertained actual vital parameter. It is provided that a target vital parameter is predetermined for the at least one actual vital parameter, and a regulating deviation between the target vital parameter and the at least one actual vital parameter is ascertained, wherein the at least one vehicle comfort function is controlled and/or regulated depending on a regulating deviation. Printed publication DE 10 2017 001 320 A1 further describes a device for operating a vehicle.

Exemplary embodiments of the invention are directed to an improved method for signaling vital parameters and/or vital parameter patterns for a vehicle occupant in a vehicle.

In a method for signaling a measured and/or a predetermined vital parameter and/or vital parameter pattern for a vehicle occupant in a vehicle, at least one functional element is arranged in the vehicle interior and is set up for a visual, audible, and/or haptic effect on at least one vehicle occupant.

According to the invention, a measured and/or predetermined vital parameter and/or a measured and/or predetermined vital parameter pattern is signaled to a vehicle occupant in a non-verbal manner by means of the at least one functional element.

Vital parameters are measured values describing basic functions of the human body, for example heart frequency or heart rate, blood pressure, body temperature, or breathing rate. A structured arranged plurality of such measured values is referred to as a vital parameter pattern. For example, a vital parameter pattern can be specified by the sequence of measured values of a single vital parameter, for example breathing frequency, over a predetermined period of time. A vital parameter pattern can also be specified by a plurality of measured values, which are allocated to different vital parameters and are recorded at a single common point in time. For example, the breathing frequency, the heart rate, and the body temperature at a point in time can constitute a vital parameter pattern.

Vital parameters are based on a state of a physiological system generating the vital parameters, which is referred to as a vital state. A vital state that is strained in comparison to a reference state is referred to as stress or a stress state.

The signaled vital parameter or the signaled vital parameter pattern can be predetermined as the target value independent of the vital state of a vehicle occupant. For example, a vehicle occupant can be encouraged to take a long and deep breath by a breathing frequency being signaled in a lower (slow) range of physiological tidal breathing.

The vital parameter or the vital parameter pattern can also be signaled corresponding to a measurement undertaken in a vehicle occupant. For example, a heart rate can be ascertained in a ballisto-cardiographic manner by a camera arranged in the vehicle interior and directed towards the face or the lips of a vehicle occupant and can be signaled by means of the at least one functional element. It is also possible for the vital parameter ascertained or the vital parameter pattern ascertained to be compared to a reference value and a deviation from this to be signaled by means of the at least one functional element.

For example, a stress state of a vehicle occupant can be recognized by an increased heart rate and/or an increased breathing rate and/or reduced heart rate variability. Consequently, a vehicle occupant can be guided to a state with reduced stress by signaling a slow, deep breath. Such methods for influencing the vital state in which information or instructions are presented verbally, i.e., as spoken or written word, are known from the prior art as bio-feedback methods.

According to the invention, the signaling of the vital state (by signaling vital parameters or vital parameter patterns) or the signaling of instructions for influencing the vital state (the bio-feedback) is carried out in a novel manner in comparison to the prior art non-verbally by means of the at least one functional element arranged in the vehicle interior.

It is known that the processing of verbally present information is accompanied by a cognitive load, which reduces the attention, reaction speed, and handling ability of a vehicle occupant, in particular a driver. It is thus an advantage of the method according to the invention that the vital state of a vehicle occupant can be improved, wherein the attention, reaction speed, and handling ability of the vehicle occupant is not negatively impacted or to a lesser extent in comparison to methods according to the prior art. The method according to the invention thus makes it possible to drive vehicles in road traffic in a safe and simultaneously relaxed manner.

In an embodiment of the method, a vehicle occupant sets a breathing frequency. Then, according to the breathing frequency set, the point in time and/or the course of a recommended inspiration and/or a recommended expiration is signaled. Using this embodiment, the breathing of a vehicle occupant can be influenced in a simple manner and their relaxation thus facilitated.

In an embodiment of the method, at least one vital parameter and/or vital parameter pattern of a vehicle occupant is ascertained in a first step and is compared to a vital parameter or vital parameter pattern typical of a relaxed state. In a second step, the degree of accordance between the measured vital parameter or vital parameter pattern and the vital parameter or vital parameter pattern typical of a relaxed state is signaled non-verbally by means of a functional element arranged in the vehicle interior that acts visually and/or audibly and/or haptically on the vehicle occupant.

An advantage of this embodiment is that a piece of feedback about a change of their vital state is emitted to the vehicle occupant. Thus, the vehicle occupant learns to consciously control their vital state. For example, the vehicle occupant can control their breathing in such a way that calmness and relaxation emerge. In addition, attention is not or only marginally distracted from traffic occurrences as a result of the non-verbal signaling according to the invention.

In an embodiment of the method, a heart rate is ascertained as a vital parameter and, from this, a level of heart rate variability is determined. The heart rate variability determined is compared to a level of heart rate variability typical of a relaxed state.

The inverse of the spacing apart of two successive R-waves in a QRS complex of the electrocardiogram is referred to as heart rate. The methods for determining the heart rate variability from the heart rate are known from the prior art. For example, the moving averaged variance of the heart rate can be used as a measure of heart rate variability.

Heart rate variability is a particularly specific and sensitive measure of the degree of tension and relaxation. This embodiment of the method thus allows a particular sensitive and exact control of the vital state of a vehicle occupant.

In an embodiment of the method, at least one massage element and/or a lumbar support that can be shifted in a dorsal-ventral direction is arranged on at least one vehicle seat. A measured and/or a predetermined vital parameter and/or vital parameter pattern is signaled by setting the massage element and/or by adjusting the lumbar support.

For example, a vehicle occupant sitting on a vehicle seat can be taught to breathe in by the lumbar support being moved in the dorsal direction initially quickly and then gradually getting slower. Teaching them to expire is carried out by the lumbar support being moved in the opposite, i.e., ventral, direction firstly quickly and then gradually getting slower.

An advantage of this embodiment of the method is that a continuous and thus more exact and finer control of the vital state of a vehicle occupant is possible. Thus, the vehicle occupant also learns how to bring about a relaxed state in an easy, quick, and reliable manner.

In an embodiment of the method, a plurality of loudspeakers is arranged and set up in the interior of the vehicle for a quadrophonic sound reproduction. Signaling a measured and/or a predetermined vital parameter and/or vital parameter pattern is carried out by pre-producing a quadrophonic sound signal (4D sounds) by means of the loudspeakers.

An advantage of this embodiment is the particularly simple feasibility and the particularly good perception of 4D sounds by vehicle occupants. In addition, it is particularly simply possible to influence the vital state of a plurality of vehicle occupants.

In an embodiment of the method, at least one interior light that can be changed in terms of light intensity and/or light color is arranged in the vehicle interior. The signaling of a measured and/or a predetermined vital parameter and/or vital parameter pattern is carried out by changing the light intensity and/or the light color of the at least one interior light.

For example, lighting situations of the vehicle interior referred to as ambient lighting or as connected lighting are known from the prior art, which can be changed easily and can be set with the present means. This embodiment is thus particularly well suited to a simple feasibility of the method.

In an embodiment of the method, an air-conditioning system having an air outlet opening arranged in the vehicle interior is arranged in the vehicle, which is set up to emit an airflow that can be changed at least in terms of temperature and/or in terms of volume flow. The signaling of a measured and/or a predetermined vital parameter and/or vital parameter pattern is carried out by changing the temperature and/or the volume flow of the airflow emitted by the air-conditioning system via the air outlet opening.

Air-conditioning systems that can be modulated or changed in this way are known and prevalent in the prior art. An advantage of this embodiment of the method is thus that it can be implemented particular simply, in particular without additional functional elements, in a vehicle. In particular, implementation is also possible in an older vehicle without laborious conversion.

In an embodiment of the method, a steering wheel that can be made to vibrate is arranged in the interior of the vehicle. The signaling of a measured and/or a predetermined vital parameter and/or vital parameter pattern is carried out by the steering wheel being made to vibrate.

An advantage of this embodiment is that, optionally, the vital state of only the driver can be controlled without influencing, impeding, or bothering other vehicle occupants in terms of their vital parameters.

In an embodiment of the method, at least one seatbelt than can be changed at least in terms of belt tension and or in terms of belt setting can be arranged in the vehicle interior. The signaling of a measured and/or a predetermined vital parameter and/or vital parameter pattern is carried out by changing the belt tension and/or the belt setting of the seatbelt.

An advantage of this embodiment is that, optionally, the vital state of a vehicle occupant can be controlled without influencing, impeding, or bothering other vehicle occupants in terms of their vital parameters. In particular, different vehicle occupants can be influenced simultaneously in different ways in terms of their vital parameters.

BRIEF DESCRIPTION OF THE SOLE FIGURE

Exemplary embodiments of the invention are explained in more detail below by means of a drawing.

The sole FIGURE schematically illustrates a vehicle interior.

DETAILED DESCRIPTION

The sole FIGURE illustrates a vehicle interior 1 of a vehicle in which functional elements 2 to 9 are arranged, with which safety and vehicle comfort functions are implemented.

A steering wheel 2 is arranged in the vehicle interior 1, which can be made to vibrate by means of electromechanical actuators (not depicted in more detail). Furthermore, intelligent interior lights 3 are arranged in the vehicle interior 1, which can be varied in terms of light intensity and/or in terms of light color. For example, a plurality of interior lights 3 can be controlled synchronously in order to convey a predetermined lighting impression in the vehicle interior 1, for example an ambient light lighting impression or a connected light lighting impression.

In addition, loudspeakers 4 are arranged in the vehicle interior 1, which are set up for reproducing 4D sound.

Furthermore, vehicle seats 5 are arranged in the vehicle interior 1. A vehicle seat 5 has massage elements 6 that can be operated electromechanically and/or pneumatically, which are set up for locally moving seat elements of the vehicle seat 5 in such a way that a massage function is implemented for a person sitting on the vehicle seat 5. The massage elements 6 can be formed, for example, as air-filled cushion elements which change in terms of their shape by means of pneumatically varied inner pressure and exert a massage movement on a partial surface of the seat surface or the backrest of the vehicle seat 5.

Moreover, the vehicle seat 5 has an electromechanically moveable lumbar support 7 in the backrest, with which a support and pressure effect can be exerted on the lumbar spine of a person sitting on the vehicle seat 5 with shiftable intensity.

Furthermore, seatbelts 8 for safely fixing a person sitting on a vehicle seat 5 are arranged in the vehicle interior 1. The seatbelts 8 can be changed in terms of belt setting and/or in terms of belt tension, for example by means of electromechanical drives not depicted in more detail.

Furthermore, the vehicle interior 1 has at least one air outlet opening 9 for the vehicle air-conditioning, from which air flow with an air flow that can be changed, for example, by adjusting a fan rotational speed and/or a temperature that can be changed flows.

The functional elements 2 to 9 can thus be perceived haptically, visually and/or audibly by a vehicle occupant and can be used to introduce bio-feedback training as described below.

In a first part of the method referred to as a breathing guideline, a vehicle occupant is made aware of the point in time of breathing in and/or the point in time of breathing out by means of the functional elements 2 to 9, wherein the vehicle occupant can set the breathing frequency controlled by the breathing guideline in a physiological breathing frequency range, for example in a range of between 5 to 12, preferably of between 5 to 7 breath cycles a minute. A breath cycle here comprises an inspiration and a successive expiration.

The guideline of the point in time for a breathing movement (inspiration or expiration) can be displayed visually, for example by text and/or drawings depicted on a display. Additionally, or alternatively, the point in time for a breathing movement can be displayed audibly, for example by an announcement reproduced via a loudspeaker 4.

According to the invention, the signaling of the point in time for a breathing movement can be supported by a massage element 6 assuming a predetermined position and/or carrying out a predetermined movement.

Additionally, or alternatively, the signaling of the point in time for a breathing movement can be supported by the lumbar support 7 being moved into a predetermined position.

Additionally, or alternatively, the signaling of the point in time for a breathing movement can be supported by an acoustic signal formed as a 4D sound being emitted via loudspeakers 4.

Additionally, or alternatively, the signaling of the point in time for a breathing movement can be supported by a quadrophonic acoustic signal formed as 4D sound being emitted via loudspeakers 4.

Additionally, or alternatively, the signaling of the point in time for a breathing movement can be supported by light emitted by at least one interior light 3 being changed in terms of the intensity and/or in terms of color.

Additionally, or alternatively, the signaling of the point in time for a breathing movement can be supported by an air-conditioning system of the vehicle being controlled in such a way that a pulsating amount of air emerges from at least one air outlet opening 9 and/or a pulsating temperature of the emerging amount of air is set.

Additionally, or alternatively, the signaling of the point in time for a breathing movement can be supported by a distinctive vibration of the steering wheel 2.

Additionally, or alternatively, the signaling of the point in time for a breathing movement can be supported by a seatbelt 8 being tensioned (tightened) or relaxed.

It is possible that the signals emitted by the functional elements 2 to 9 vary according to the type of the breathing movement signaled (inspiration or expiration) and according to the point in time in relation to the start of the breathing movement. For example, it is possible to move a lumbar support 7 during a signaled inspiration initially quickly and then gradually getting slower in the dorsal direction and, during a signaled expiration, to initially move it quickly and then gradually getting slower in a ventral direction.

The signals emitted by the functional elements in the part of the method referred to as the breathing guideline are only controlled by the chosen breathing frequency.

In a second part of the method referred to as breathing analysis, vital parameters of a vehicle occupant are recorded and analyzed. Measurements are referred to as vital parameters, which describe basic functions of the human body, for example heart frequency or heart rate, blood pressure, body temperature, or breathing frequency.

Methods for measuring such parameters are known from the prior art. For example, it is known that the heart frequency or heart rate, i.e., the number of heart beats per minute, can be ascertained via an electrocardiogram. Electrodes for extrapolating the electrocardiogram can be stitched into items of clothing, for example, or fixed on the surface of the skin by means of armbands. It is also known that the heart frequency can be ascertained ballisto-cardiographically by evaluating camera recordings of the face, in particular the lips, of a vehicle occupant. Measuring methods are also known for other vital parameters.

According to the invention, a vital parameter or a vital parameter pattern, which describes the temporal course of a vital parameter, is compared to a vital parameter or a vital parameter pattern typical of a relaxed person in the part of the method referred to as breathing analysis.

In an embodiment of the method, a level of heart rate variability is ascertained from the temporal course of the heart rate, the heart rate variability describing the fluctuation of the time intervals between the R-waves of successive QRS complexes. Methods and measurements for escribing the heart rate variability are known from the prior art. It is also known that very low heart rate variability is typical of stress situations or situations of high cognitive or emotional tension, while heart rate variability that is high in the physiological range is typical of a relaxed base mood.

From the comparison between the measured vital parameter or vital parameter pattern and a vital parameter or vital parameter pattern typical of a relaxed person, a current degree of accordance with the vital parameter typical of a relaxed person or the vital signal typical of a relaxed person is ascertained. Preferably, the degree of accordance is ascertained as ordinal-scaled variables or as metric variables. For example, an ordinal-scaled degree of accordance can range from a category of "currently, the pattern of the vital parameter matches a typical pattern of a relaxed person very well" to a category of "currently, the pattern of the vital parameter deviates significantly from the pattern of a relaxed person".

The ascertained degree of accordance between the measured vital parameter or vital parameter pattern and a vital parameter or vital parameter pattern typical of a relaxed person can be signaled visually, for example by lettering and/or drawings depicted on a display. Additionally, or alternatively, the degree of accordance can be signaled audibly, for example by an announcement reproduced via a loudspeaker 4.

Signaling the degree of accordance between the measured vital parameter or vital parameter pattern and a vital parameter or vital parameter pattern typical of a relaxed person can thus be supported by a massage element 6 assuming a predetermined position and/or carrying out a predetermined movement.

Additionally, or alternatively, signaling the degree of accordance between the measured vital parameter or vital parameter pattern and a vital parameter or vital parameter pattern typical of a relaxed person can be supported by the lumbar support 7 being moved into a predetermined position.

Additionally, or alternatively, signaling the degree of accordance between the measured vital parameter or vital parameter pattern and a vital parameter or vital parameter pattern typical of a relaxed person can be supported by an acoustic signal formed as 4D sound being emitted via loudspeakers 4.

Additionally, or alternatively, signaling the degree of accordance between the measured vital parameter or vital parameter pattern and a vital parameter or vital parameter pattern typical of a relaxed person can be supported by a quadrophonic acoustic signal formed as 4D sound being emitted via loudspeakers 4.

Additionally, or alternatively, signaling the degree of accordance between the measured vital parameter or vital parameter pattern and a vital parameter or vital parameter pattern typical of a relaxed person can be supported by light emitted by at least one interior light 3 being changed in terms of intensity and/or in terms of color.

Additionally, or alternatively, signaling the degree of accordance between the measured vital parameter or vital parameter pattern and a vital parameter or vital parameter pattern typical of a relaxed person can be supported by an air-conditioning system of the vehicle being controlled in such a way that a pulsating amount of air emerges from at least one air outlet opening 9 and/or a pulsating temperature of the emerging amount of air being set.

Additionally, or alternatively, signaling the degree of accordance between the measured vital parameter or vital parameter pattern and a vital parameter or vital parameter pattern typical of a relaxed person can be supported by there being a distinctive vibration of the steering wheel 2.

Additionally, or alternatively, signaling the degree of accordance between the measured vital parameter or vital parameter pattern and a vital parameter or vital parameter pattern typical of a relaxed person can be supported by a seatbelt 8 being tensioned (tightened) or relaxed.

An advantage of the method according to the invention is that the distraction of a vehicle occupant, in particular a driver, when signaling a predetermined breathing movement and/or a degree of accordance between the measured vital parameter or vital parameter pattern and a vital parameter or vital parameter pattern typical of a relaxed person can be reduced. Thus, a strong, clear, and specific guide of a vehicle occupant is possible when carrying out bio-feedback exercises, wherein, at the same time, their attention for traffic occurrences is not or only minimally impeded.

Although the invention has been illustrated and described in detail by way of preferred embodiments, the invention is not limited by the examples disclosed, and other variations can be derived from these by the person skilled in the art without leaving the scope of the invention. It is therefore clear that there is a plurality of possible variations. It is also clear that embodiments stated by way of example are only really examples that are not to be seen as limiting the scope, application possibilities or configuration of the invention in any way. In fact, the preceding description and the description of the FIGURES enable the person skilled in the art to implement the exemplary embodiments in concrete manner, wherein, with the knowledge of the disclosed inventive concept, the person skilled in the art is able to undertake various changes, for example, with regard to the functioning or arrangement of individual elements stated in an exemplary embodiment without leaving the scope of the invention, which is defined by the claims and their legal equivalents, such as further explanations in the description.

The invention claimed is:

1. A method, comprising:

measuring a vital parameter or vital parameter pattern of a vehicle occupant in a vehicle seat of a vehicle, wherein the vehicle seat includes at least one massage element or an adjustable lumbar support;

determining, based on the measuring, that the vehicle occupant is in a stress state; and non-verbally signaling the vehicle occupant a course of a recommended inspiration and a recommended expiration according to a recommended breathing frequency by shifting the at least one massage element or the adjustable lumbar support back and forth in a dorsal-ventral direction in a decreasing frequency over time until the vehicle occupant's breathing frequency is same as the breathing frequency.

2. The method of claim 1, wherein the measured vital parameter or vital parameter pattern is compared to a reference vital parameter or a reference vital parameter pattern typical of a relaxed state, wherein a degree of accordance between the measured vital parameter or the measured vital parameter pattern and the reference vital parameter or the reference vital parameter pattern typical of a relaxed state is non-verbally signaled to the vehicle occupant by the at least one functional element in a visual, audible, or haptical manner.

3. The method of claim 2, wherein the measured vital parameter or vital parameter pattern is a heart rate variability determined from a heart rate of the vehicle occupant and the heart rate variability is compared to a reference heart rate variability typical of a relaxed state.

4. The method of claim 2, wherein the non-verbal signaling further comprises reproducing a quadrophonic sound signal by a plurality of loudspeakers arranged in the vehicle interior and configured for quadrophonic sound reproduction.

5. The method of claim 2, wherein the non-verbal signaling further comprises changing a light intensity or a light color of at least one interior light arranged in an interior of the vehicle.

6. The method of claim 2, wherein the non-verbal signaling further comprises adjusting an air-conditioning system arranged in the vehicle having an air outlet opening arranged in an interior of the vehicle by changing a temperature or volume of an air flow emitted by the air-conditioning system via the air outlet opening.

7. The method of claim 2, wherein the non-verbal signaling further comprises vibrating a steering wheel arranged in an interior of the vehicle.

8. The method of claim 2, wherein the non-verbal signaling further comprises changing a belt tension or a belt setting of at least one seatbelt in an interior of the vehicle in terms of belt tension or belt position.

* * * * *